US 12,175,607 B2

United States Patent
Spaas et al.

(10) Patent No.: US 12,175,607 B2
(45) Date of Patent: Dec. 24, 2024

(54) ENHANCED AUGMENTED REALITY HEADSET FOR MEDICAL IMAGING

(71) Applicant: ARSpectra S.à.r.l, Foetz (LU)

(72) Inventors: Cedric Spaas, Ghent (BE); Arnaud Legros, Foetz (LU); Arun Annaiyan, Foetz (LU); Laura Perez-Pachon, Foetz (LU)

(73) Assignee: ARSpectra S.à.r.l, Foetz (LU)

( * ) Notice: Subject to any disclaimer, the term of this patent is extended or adjusted under 35 U.S.C. 154(b) by 355 days.

(21) Appl. No.: 17/856,488

(22) Filed: Jul. 1, 2022

(65) Prior Publication Data
US 2022/0354582 A1    Nov. 10, 2022

(30) Foreign Application Priority Data

May 5, 2021    (LU) .......................................... 500127

(51) Int. Cl.
*G06T 19/00* (2011.01)
*A61B 34/10* (2016.01)
(Continued)

(52) U.S. Cl.
CPC ............ *G06T 19/006* (2013.01); *A61B 34/10* (2016.02); *A61B 90/00* (2016.02); *A61B 90/36* (2016.02); *A61B 90/361* (2016.02); *A61B 90/37* (2016.02); *A61B 90/39* (2016.02); *A61B 90/50* (2016.02); *G02B 27/0093* (2013.01); *G02B 27/0101* (2013.01); *G02B 27/017* (2013.01); *G02B 27/0172* (2013.01); *G02B 27/0179* (2013.01); *G06F 3/011* (2013.01); *G06F 3/013* (2013.01);
(Continued)

(58) Field of Classification Search
None
See application file for complete search history.

(56) References Cited

U.S. PATENT DOCUMENTS

| | | | |
|---|---|---|---|
| 10,729,410 B2 * | 8/2020 | Dufour | ................ A61B 8/5215 |
| 2011/0152692 A1 * | 6/2011 | Nie | ....................... A61B 5/7425 |
| | | | 600/473 |

(Continued)

FOREIGN PATENT DOCUMENTS

| | | |
|---|---|---|
| GB | 2588774 | 11/2019 |
| KR | 20180136219 A | 12/2018 |
| WO | WO2021089440 A1 | 5/2021 |

OTHER PUBLICATIONS

Mondal Suman B et al.; "Optical See-Through Cancer Vision Goggles Enable Direct Patient Visualization and Real-Time Fluorescence-Guided Oncologic Surgery"; Annals of Surgical Oncology; New York; Feb. 17, 2017.

(Continued)

*Primary Examiner* — Jwalant Amin
(74) *Attorney, Agent, or Firm* — Dickinson Wright PLLC; Nicholas P. Coleman (57) ABSTRACT

An augmented reality, AR, system (100) for use in a medical procedure is disclosed. The AR system (100) comprises an AR headset (2), and a processor (12). The AR headset (2) comprises a camera (6a, 6b), a near eye display (4a, 4b) and a depth sensor (10a, 10b). The processor (12) is configured to adjust the position of the image obtained by the camera (6a, 6b) on the display (4a, 4b) throughout the medical procedure based on changes in the distance measured by the depth sensor (10a, 10b).

15 Claims, 9 Drawing Sheets

(51) Int. Cl.
*A61B 90/00* (2016.01)
*A61B 90/50* (2016.01)
*G02B 27/00* (2006.01)
*G02B 27/01* (2006.01)
*G06F 3/01* (2006.01)
*G06T 7/70* (2017.01)
*G06T 7/80* (2017.01)
*G06T 19/20* (2011.01)
*H04N 13/239* (2018.01)
*H04N 13/271* (2018.01)

(52) U.S. Cl.
CPC .............. *G06T 7/70* (2017.01); *G06T 7/80* (2017.01); *G06T 19/20* (2013.01); *H04N 13/239* (2018.05); *H04N 13/271* (2018.05); *A61B 2034/105* (2016.02); *A61B 2034/107* (2016.02); *A61B 2090/365* (2016.02); *A61B 2090/371* (2016.02); *A61B 2090/372* (2016.02); *A61B 2090/3941* (2016.02); *A61B 2090/395* (2016.02); *A61B 2090/502* (2016.02); *A61B 2562/0257* (2013.01); *G02B 2027/0127* (2013.01); *G02B 2027/0134* (2013.01); *G02B 2027/0138* (2013.01); *G02B 2027/014* (2013.01); *G02B 2027/0187* (2013.01); *G06T 2210/41* (2013.01); *G06T 2219/2004* (2013.01)

(56) References Cited

U.S. PATENT DOCUMENTS

| | | | |
|---|---|---|---|
| 2015/0085087 A1* | 3/2015 | Vienne | H04N 13/144 |
| | | | 348/51 |
| 2019/0050665 A1 | 2/2019 | Sakuragi | |
| 2019/0310705 A1* | 10/2019 | Hincapie Ramos | H04N 13/332 |
| 2022/0138998 A1* | 5/2022 | Rege | A61B 90/20 |
| | | | 345/633 |
| 2022/0391013 A1* | 12/2022 | Vlaskamp | G02B 6/0076 |

OTHER PUBLICATIONS

Bajura M et al.; "Merging Virtual Objects with the real world: Seeing Ultrasound Imagery within the Patient"; Computer Graphics; Jul. 1, 1992.

* cited by examiner

ENHANCED AUGMENTED REALITY HEADSET FOR MEDICAL IMAGING

This application claims priority to Luxembourg Patent Application LU500127 filed on May 5, 2021, the disclosure of which is hereby incorporated by reference.

FIELD

The present invention relates to augmented reality system for use in medical procedures.

BACKGROUND

Fluorescence-based intra-operative surgical guidance is becoming a widely used procedure. This growth is especially focused on clinical approaches with indocyanine green (ICG) as the fluorescent marker, detected in the near-infrared spectrum (NIR).

Several medical imaging devices have been commercialized to allow ICG-based guidance in surgery. The approach is used for blood flow assessment, vessel patency, perfusion evaluation (especially in reconstructive and bypass surgeries), lymphatic imaging, and surgical procedures as sentinel lymph node identification and mapping. Further research efforts target the potential for imaging molecular tracers that report on new vascular, structural, metabolic, immunologic, or genetic features of the tissue. The application rates and range of ICG in medical procedures are growing rapidly.

The process involves injecting the fluorophore just before the surgical procedure. Near-infrared light is then shone onto the target area exciting the molecular ligands, which in response emit light with a specific wavelength. A camera sensitive to this range of the light spectrum is then used to detect the light to form an image which clearly denotes the target tissues.

This approach allows to significantly improve the detection and removal of primary tumour nodules of various cancer types as well as lingering metastases in sentinel lymph nodes, for instance in lung cancer surgery. Other uses include use in breast cancer surgery with lumpectomy or mastectomy and planned auxiliary sentinel node biopsy procedures.

Current systems are based on a mobile camera unit that acquires the emitted light with the visualisation of the detected image on an external screen next to the operation table. During the procedure the surgeon has to remove their focus from the area of the patient on which they are operating and subjectively compare the displayed data taken from a different point of view, with their real world view of the patient's actual body. This continuous comparative action makes fluorescence imaging cumbersome and especially limits its ability to accurately map the fluorescence-labelled tissues displayed with what the surgeon can see. In this latter subjective step, despite excellent professional training, significant amounts of precision, completeness, concentration, and time-efficiency are lost.

It is desirable to have a way in which the detected view of the target tissue through fluorescence imaging can be more easily and accurately correlated with the surgeon's actual real world view of the patient. This could lead to the prospect of making the procedure quicker and less prone to human error.

SUMMARY OF INVENTION

According to an aspect, there is provided an augmented reality, AR, system for monitoring a target in a medical procedure. The AR system comprises an optical contrast agent within the target, at least one light source for illuminating the target, the or each light source having a wavelength adapted to excite the optical contrast agent, an AR headset and a processor. The AR headset comprise imaging means configured to detect light from at least the agent within the target, a near-eye display positioned between a wearer's eyes and the target, the display configured to display an image of the at least agent based on the light detected by the imaging means, such that the image overlays a wearer's view of the target and a depth sensor, configured to determine a distance between the headset and the target throughout the medical procedure. The processor is configured to determine a mismatch between the image of the target obtained from the imaging means and the wearer's view of the target based on the value of the distance measured by the depth sensor, a distance between a surface of the target and the agent, and a position of the wearer's eyes; to determine the mismatch required for the wearer to perceive the images from the imaging means as a 3D object/volume/shape from the determined distance and the position of the wearer's eyes; to adjust the position of the image on the display such that it is corrected based on the determined mismatch such that the image matches the wearer's view of the target; and to repeat the determination of the mismatch and the adjustment of the position of the image throughout the medical procedure to take into account changes in the distance measured by the depth sensor throughout the medical procedure.

By displaying the image of the target in a display of an augmented reality device, the wearer performing the medical procedure is provided with the view of the image generated by the light from the target in their direct line of sight. With light detected from an optical contrast agent within the target, at a wavelength preferably transparent to various skin and organ tissues, wherein such surface tissues become transparent to the imaging means, the wearer is advantageously provided with a subcutaneous view of the target, moreover substantially in real-time.

The difference between the position of the wearer's eyes and the distance to the target enables the discrepancy between the views to be adjusted for. This is because the camera will not have the same view as the wearer's view of the target. This correction is performed throughout the procedure through the depth sensor measuring the distance between the headset and the target. This allows for a dynamic updating of the position of the augmented image on the display such that the image that is displayed is at the correct position such that it overlaps the wearer's real world view of the target. This ensures that the augmented image in the display matches the exact position on the target from which it was emitted in the wearer's view.

This can provide the medical professional wearing the headset with an accurate mapping between the augmented generated image and the actual patient. This can enable a much greater precision when carrying out a surgical procedure on the patient.

Preferably, the processor is further configured to determine the mismatch between the image of the target obtained from the imaging means and the wearer's view of the target by being configured to assign a position in space to act as an origin of a coordinate system; to generate a 3D model of the agent within the target based on the light detected by the imaging means; to determine the position and orientation of the target relative to the coordinate system origin based on the distance measured by the depth sensor; to determine the position of the wearer's eyes relative to the coordinate system origin; and to determine the position and orientation of the headset relative to the coordinate system origin.

By determining the position and orientation of the headset, and the target and the position of the wearer's eyes, with respect to an origin of a coordinate system their position and orientation are transformed into a defined coordinate system with respect to one another. This allows the relative positioning of the image of the target on the display to be adjusted through the geometric relationships between the wearer's eyes and the headset with respect to the target through the continually updated measurement of the distance to the target. In addition to the position of the wearer's eyes the orientation of the wearer's eyes may also be determined.

The origin of a coordinate system may be on the headset. For instance, it may be located at a point between where the wearer's eyes would be located. Alternatively, it may be set as the point where the camera, depth sensor or display is located on the headset. The origin of a coordinate system need not be on the headset and may instead be a point that is external to the headset. The origin of a coordinate system may be a position in 3D space represented in 3D coordinates. The position and orientation of the wearer's eyes, the target, and the headset may be converted to 3D coordinates.

The position and orientation of the headset relative to the origin of a coordinate system may be the position and orientation of at least one of a display, a depth sensor, and a camera. The positioning of the display, camera and/or depth sensor relative to each other may be known. This allows the displacement between each of these to be taken into account when adjusting the position of the image. As their positions relative to each other may be static they may be known. The processor may receive these position values. For instance, they may be stored in memory. When the origin of a coordinate system is a position on the headset the distance between the display, depth sensor and camera relative to the origin of a coordinate system may be known from knowing the geometry of the headset.

Alternatively, if not already known the value of these positions and orientations may be measured through one or more sensors.

Preferably, the processor is further configured to adjust the position of the image on the display such that it is corrected based on the determined mismatch by being configured to set the position of the 3D model of the target relative to the coordinate system origin; to render the 3D model of the target to form the adjusted image based on the determined positions and orientations of the target, and headset and the position of the wearer's eyes; and to display the adjusted image on the display.

In this way, the generated 3D model of the target is within the same frame of reference as the headset and wearer's eyes. This enables rendering of the 3D model of the target such that the image displayed on the display takes into account the position of the headset, target and wearer's eyes.

Preferably, the imaging means comprises a plurality of cameras arranged into a stereoscopic imaging means. This arrangement advantageously permits depth and scale information to be determined rapidly and inexpensively, by exploiting the parallax between the camera's respective fields of view.

Preferably, the processor is further configured to calculate the mismatch required for the wearer to perceive the images from the stereoscopic imaging means as a 3D object. The mismatch may be determined based on the determined distance to the target. It may be also determined based on the position of the wearer's eyes. This may be based on the interpupillary distance (IPD), and/or the distance between the headset and the wearer's eyes. Preferably, the processor is further configured to calculate the mismatch between the image of the target obtained from the camera and the wearers view of the target by being configured to: determine the mismatch required for the wearer to perceive the images from the stereo system as a 3D object from the determined distance and the position of the wearer's eyes.

This enables the alignment of the generated image in the display to be updated such that it matches the wearer's view of the target for each of the wearer's eyes and provide a depth perception to the wearer. The adjustment of the image in the display may be different for each of the wearer's eyes.

In some aspects the AR headset may further comprise an eye tracking sensor, the eye tracking sensor configured to continually determine the position of the wearer's eyes throughout the medical procedure, such that the repetition of the determination of the mismatch and the adjustment of the position of the image throughout the medical procedure takes into account changes in the position of the wearer's eyes throughout the medical procedure.

In this way, the position of the wearer's eyes throughout the medical procedure can be tracked and used to update the position of the generated image in the display. Throughout the medical procedure the position of the wearer's eyes will not be fixed with their view and gaze varying throughout the procedure. The accuracy of the positioning of the generated image over the wearer's view can be improved by the continual determination of the position of the wearer's eyes and their position relative to the target and the headset. The eye tracking sensor may be configured to also determine the orientation of the wearer's eyes throughout the medical procedure.

The eye tracking sensor may also determine the focus of the wearer's eyes, i.e. the position of where they are focusing on at any particular time. In this way the generated image can be displayed such that it is displayed in focus at all time in the wearer's view of the target.

The eye tracking sensors may be a plurality of eye tracking sensors. For instance, there may be at least a single sensor that tracks each eye. Alternatively, a single tracking sensor may track the position of both eyes.

The eye tracking sensors may be an IR light source that scans the position of each eye to determine its position. This may be in the form of an LED or laser. Alternatively, or in addition, the eye tracking sensor may be an electric potential eye tracking sensor. The electric potential eye tracking sensor uses electrodes placed around the eye to measure the movement of the eye.

The processor may receive the position of the wearer's eyes. Preferably, the processor is further configured to obtain the position of the wearer's eyes through obtaining the interpupillary distance of the wearer's eyes.

The interpupillary distance is the distance between the pupils of each of the wearer's eyes. Each user will have an interpupillary distance that is unique to them. By knowing the interpupillary distance it can be used to determine the relative position of the wearer's eyes relative to the headset and/or the origin of a coordinate system. It can also be used to determine the mismatch required for the wearer to perceive the images from the stereo system as a 3D object. This can help position the generated image on the display at the correct position for each of the wearer's eyes overlaying each eye's view of the target.

The interpupillary distance may be obtained automatically by the processor. This may be through the use of eye tracking sensors. Alternatively, the wearer may manually provide the interpupillary distance to the processor. For instance, the wearer, or someone else, may have measured the interpupillary distance manually. Alternatively, the position of the wearer's eyes may be determined by a means other than using the interpupillary distance.

As outlined above, the position of the wearer's eyes may be determined using the eye tracking sensor. This might be the position of the wearer's eyes with respect to a origin of a coordinate system, such as a point on the headset. Alternatively, the position of the wearer's eyes relative to the origin of a coordinate system may be determined through a calibration procedure. This may be performed before the medical procedure, or if it is determined during the medical procedure that a further calibration is necessary. This calibration may involve the wearer viewing an external marker. Adjustments can then be made until the position of the image of the marker is matched to the wearer's view of the marker.

This may involve the wearer manually adjusting parameters of the image generation such that the image of the marker is moved to overlay their view of the marker. The marker may be any type of marker including a dot, or line, or a reference pattern with a known shape. This calibration enables the processor to determine the position and/or orientation of the wearer's eyes relative to the origin of a coordinate system.

Preferably, the imaging means comprise the depth sensor. Alternatively, the imaging means and the depth sensor may be separate sensors.

The depth sensor may be a time of flight depth sensor and/or the sensor may be a depth sensor. Alternatively, the depth sensor may be a stereo camera system, a LIDAR sensor, a RADAR sensor. The depth sensor may be a sensor with the sole purpose of determining distance. Alternatively, the depth sensor may be a camera that is configured to perform the role of a depth sensor. For instance, the camera and the depth sensor might be the same. In this way the camera acts both as the camera and the depth sensor. Alternatively, there may be a plurality of cameras that act as the depth sensor.

The light source may be configured to transmit light towards the target such that when subsequently detected by the camera it forms an image representative of the target or a portion thereof. The light source may be fluorescence light source. Alternatively, the light source may be such that the image is formed through reflection of the light from the target.

The AR headset may comprise the light source. Having the light source on the headset may enable the camera and the light source to be focused on the same area of the target. This ensures that the wearer has control over the illumination of the light on the target. Alternatively, the light source might be an external light source that is not located on the headset.

Preferably, the wavelength of the light is near infra-red light. The medical procedure may be a fluorescence based guidance procedure. Near infra-red light can be used for fluorescent based guidance procedures. The light source may be configured to emit within these bands. The wavelength of the NIR light may be in the order of 780 nm. This is the excitation range for ICG. However, other wavelengths of NIR may be used depending on the molecular marker being used, in a range of substantially 750 nm to 2500 nm.

The imaging means may be configured to detect in the range of wavelengths that the molecular marker being used emits within the target. This range of wavelengths depends on the type of tissue, for example, this range of wavelengths may be 825 to 860 nm for ICG when it bonds to plasma proteins. The camera may be configured to detect the same wavelength band of light as the light source.

A choice of optical contrast agent is preferably made in combination with the light detection capacity of the camera. The invention is compatible with a wide variety of optical contrast agents, such as natural metalloproteins, an example of which haemoglobin, engineered metalloproteins, cyanine dies like indocyanine green (ICG) and methylene blue (MB). Many more compounds are compatible, which include, non-exhaustively, 5-ALA PpIX—5-aminolevulinic acid protoporphyrin, 5-ALA/HAL-induced PpIX (PpIX5-ALA or PpIXHAL), fluorescein, fluorocoxib A, OBP-401 green fluoresceent protein (GFP)-expressing adenovirus, Cy5, Cy7, IRDye800CW, IRDye 700DX, S0456, SGM-10117, ZW800-I, BM-104, Folate-FITC, EC17, OTL38, cGlu-HMRG and LUM015.

The camera may detect the light continuously throughout the medical procedure. In other arrangements the camera may be arranged to acquire light at time periods that are spaced throughout the medical procedure. In this way, the generated image in the AR display can be updated through the procedure.

In other embodiments, the image detected by the camera may be captured once during the medical procedure. This image may then not be updated throughout the procedure, only its position on the near eye display to account for changes in the position of the headset. This may be the case where it not expected that the image of the target acquired by the camera will change.

The processor may be further configured to convert the light detected by the camera into an image that is visible to the user. When the light that is emitted from the target is in the IR or NIR band, the wearer's eyes would traditionally not be able to view the light. This may be the case when the light is excited through fluorescence from the target. By converting the light, and displaying the image on the near eye display, it can be displayed in a way that the wearer can visualise the light reflected from the target. This image enhances the view of the wearer providing information that they could not previously see in their line of sight.

The near eye display may be a single display. Alternatively, the near eye display may be two displays, one display for displaying an image for each eye. The near eye display may be a waveguide. Alternatively, the display might be a beam splitter display, or a laser reflection display. The display may utilise mirrors to project the image into the wearer's view. The display may be made of glass and/or plastic. In this way it is transparent. The near eye display may be alternatively a lens. Or the near eye display may be a beam that projects the image into the eyes of the wearer such that the image is displayed on the retina. In this way the near-eye display may be a virtual retinal display.

The display and/or camera may comprise one or more filters. The filters may be configured to improve the detection of the specific wavelengths of light from the target, while removing the other signals at undesired wavelengths. Alternatively, or in addition, the filters may be positioned in front of the light source.

According to a further aspect there is provided a method of adjusting the position of an image in an augmented reality (AR) system for use in a medical procedure, the AR system comprising an optical contrast agent, at least one light source, an AR headset with imaging means, depth sensor and a processor. The method comprises the steps of illuminating a target containing an optical contrast agent with the or each light source, the or each light source having a wavelength suitable for exciting the agent; detecting light from the excited agent in the target with the stereoscopic imaging means; determining a distance between the headset and the target with depth sensor throughout a medical procedure; displaying on a near-eye display positioned between a wearer's eyes and the target, an image of the target based on the detected light, such that the image overlays a wearer's view of the target in the headset, through the steps of determining a mismatch between the image of the target obtained from the imaging means and the wearer's view of the target based on the value of the determined distance, a distance between a surface of the target and the agent and a position of the wearer's eyes; determining the mismatch required for the wearer to perceive the images from the imaging means as a 3D object/volume/shape from the determined distance and the position of the wearer's eyes; and adjusting the position of the image on the display such that it is corrected based on the determined mismatch.

In an embodiment of the method, the step of determining the mismatch may comprise the further steps of assigning a position in space to act as an origin of a coordinate system; generating a 3D model of the agent within the target based on the light detected by the imaging means; determining the position and orientation of the target relative to the coordinate system origin based on the distance measured by the depth sensor; determining the position of the wearer's eyes relative to the coordinate system origin; and determining the position and orientation of the headset relative to the coordinate system origin.

In an embodiment of the method, wherein the imaging means comprises a plurality of cameras arranged into a stereoscopic imaging means, the step of determining the mismatch may also or alternatively comprise the further step of determining the mismatch required for the wearer to perceive images from the stereoscopic imaging means as a 3D object from the determined distance and the position of the wearer's eyes.

According to a further aspect there is provided a non-transitory computer readable medium, that when executed on a processor is configured to perform the above methods.

DETAILED DESCRIPTION

Figure 1:
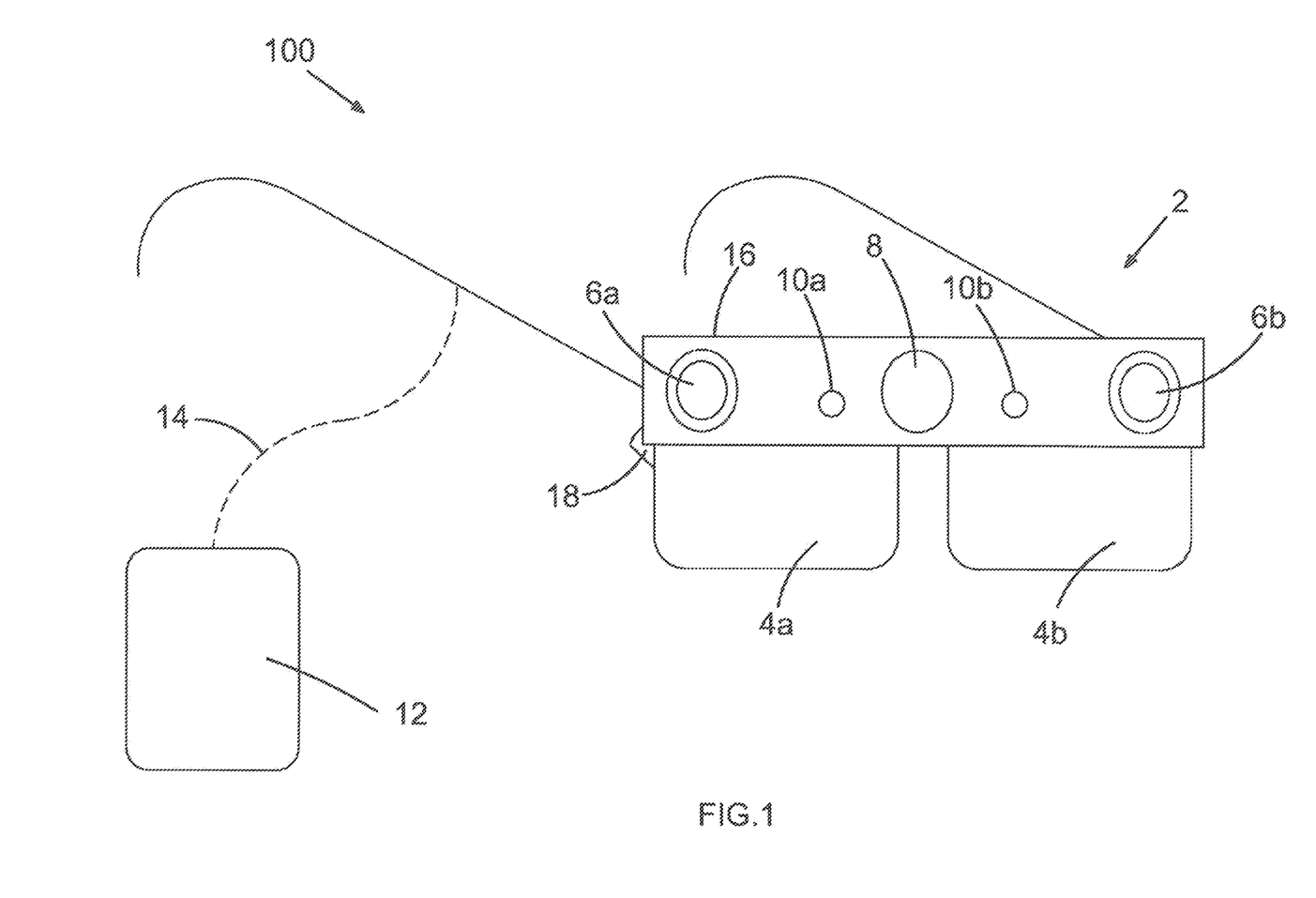
FIG. 1 shows an example augmented reality (AR) system according to the present invention.

FIG. 1 shows an augmented reality (AR) system 100 according to an embodiment of the present invention. The AR system 100 includes an AR headset 2 and a processor 12.

The augmented reality headset 2 has two displays a first display 4a and a second display 4b, the first display 4a for displaying an image to the right eye of the wearer of the headset and the second display 4b for displaying an image to the left eye of the wearer of the headset 2. As an AR headset, each display 4a, 4b is substantially transparent, allowing the headset wearer to observe their environment through the display in the manner of conventional spectacles, wherein imagery generated according to the principles described herein is effectively superimposed or overlaid onto the observed environment in the wearer's field of view through each display. The displays 4a and 4b are attached to a housing 16 of the headset 2.

Located on the housing 16 of the headset are two cameras 6a 6b. Camera 6a is located above the first display 4a, and camera 6b is located above the second display 4b. The cameras 6a 6b are capable of detecting near infrared (NIR) light.

Also located on the housing 16 is a light source 8. The light source 8 is NIR light source configured to emit NIR light in a user-selectable wavelength range of 750 nm to 2500 nm, for instance 780 nm. The light source 8 is located between the camera 6a and 6b, although it could be located at any position on the AR headset 2. Alternatively, the light source 8 may be located external to the AR headset 2.

Two depth sensors 10a and 10b are located on the housing 16 of the headset 2. The depth sensors are time of flight sensors configured to determine a distance to an object from the headset 2, and its shape and volume.

The headset 2 further includes an eye tracking sensor 18. The eye tracking sensor is located on the side of the headset that faces the head of the wearer. The eye tracking sensor is configured to determine the position of the eyes of the wearer of the headset 2.

The processor 12 is located externally to the AR headset 2. The processor may be a processor of a computer or other data processing device. The AR headset 2 is connected to the processor 12 through cable 14. The cable 14 is for sending signals between the headset and the processor 12. For instance, the data obtained from the cameras 6a 6b, eye tracking sensor 18, and depth sensors 10a 10b may be sent through cable 14 to the processor 12. The cable 14 also is for sending communication signals between the processor 12 and the headset 2 to control the camera 6a 6b, depth sensor 10a 10b, light source 8, and eye tracking sensor 18 to perform their functions.

Figure 2:
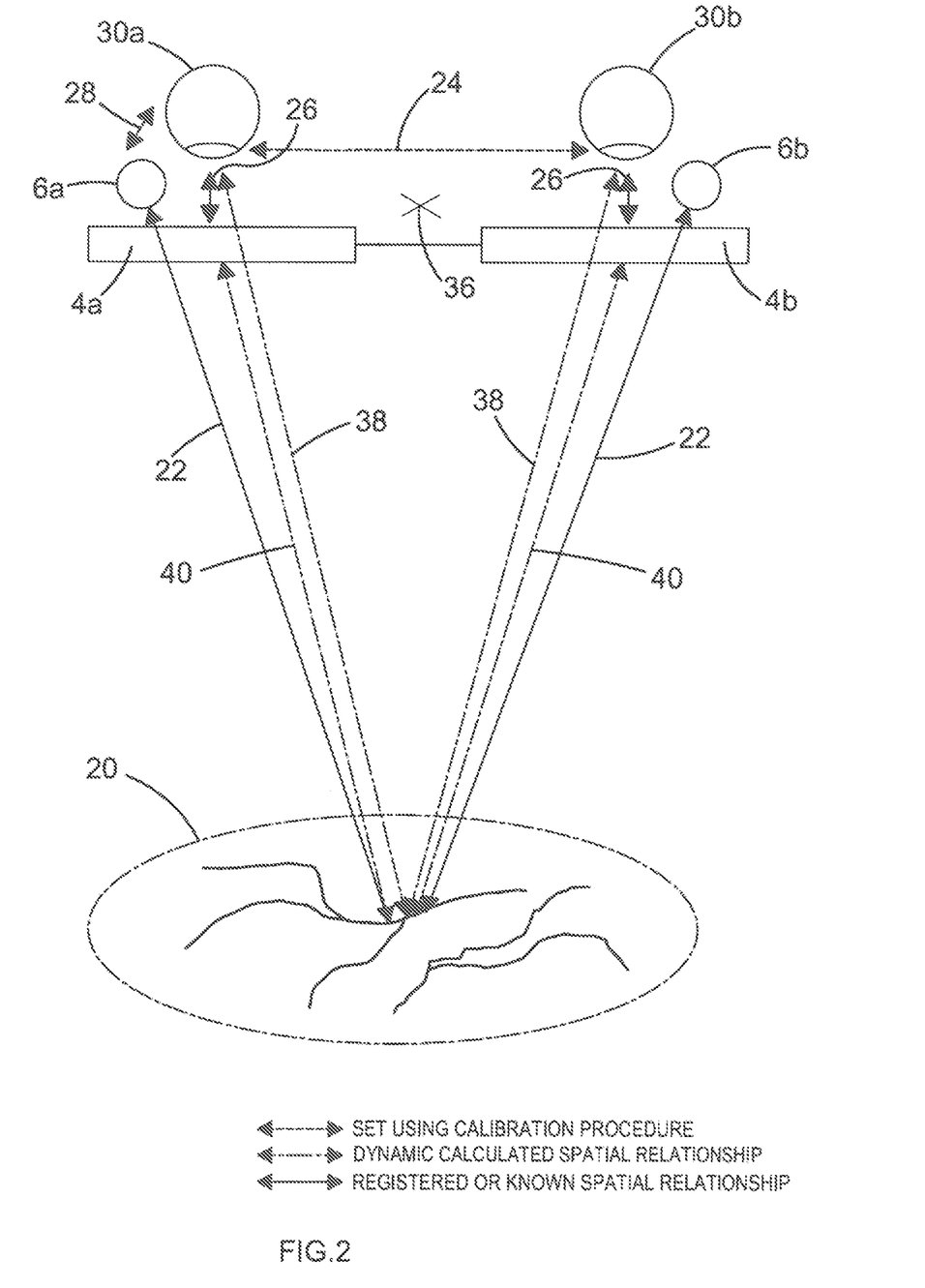
FIG. 2 shows a top down schematic view of an example AR system according to the present invention.
Figure 4:
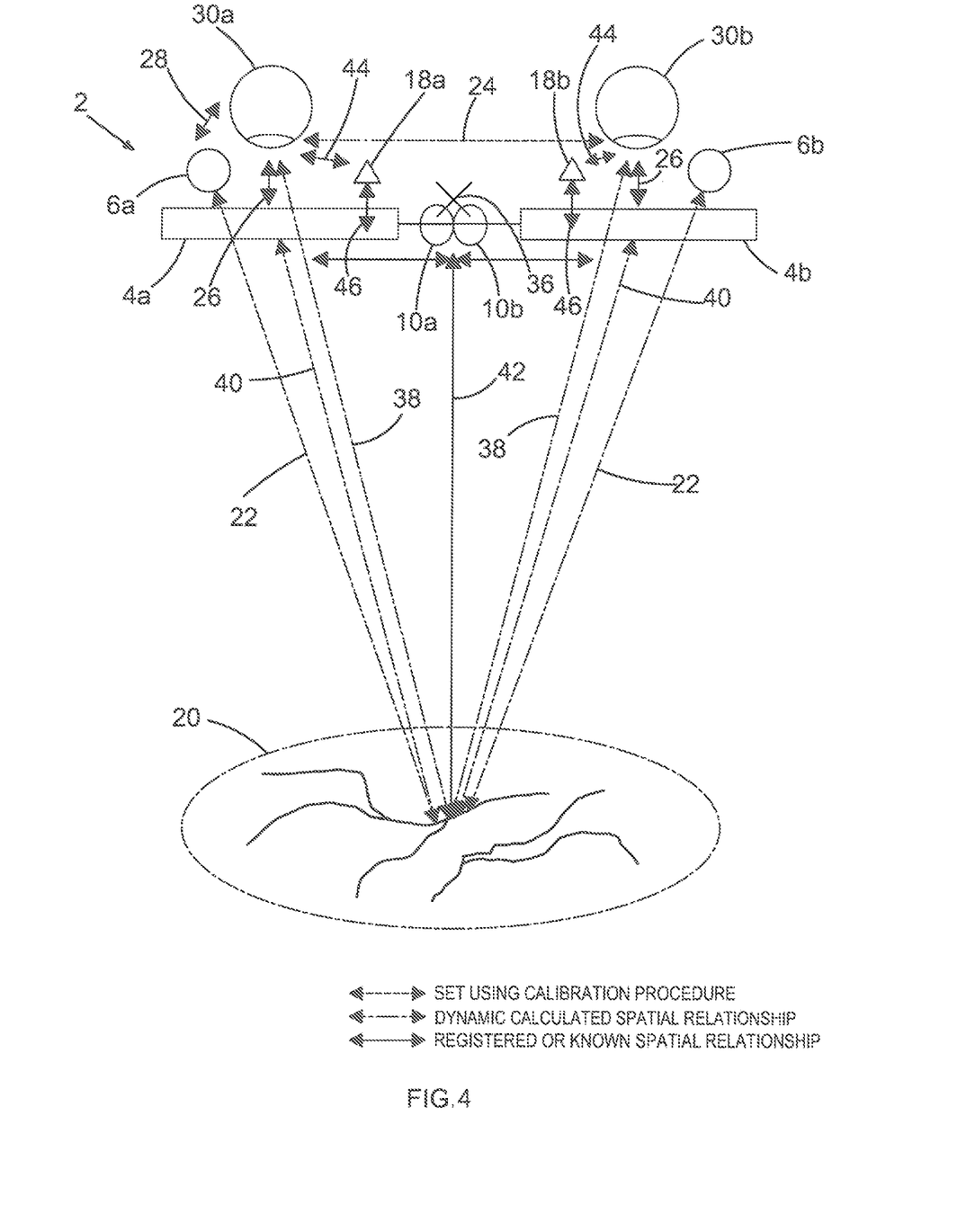
FIG. 4 shows a top down schematic view of a further example AR system according to the present invention.

FIGS. 2, and 4 show top down schematic views of the AR headset 2 according to the present invention, each Figure showing a headset 2 having a different arrangement of sensors to each other. The headset 2 is shown as being used in a fluorescence based guidance procedure.

The features of the AR headsets 2 illustrated in FIGS. 2 and 4 are illustrated with the same reference numerals to those illustrated in FIG. 1. The portion of the target 20, in this case the patient, from which the fluorescence image is being detected is also shown.

FIG. 2 shows an AR headset having two cameras 6a and 6b in stereoscopic configuration. The headset shown in FIG. 2 does not have a separate depth sensor. The two cameras 6a and 6b jointly perform the function of the depth sensor, in addition to detecting the light from the target 20 to form the images.

Shown on FIG. 2 are the spatial relationships that are determined and used to adjust the position of the image that is generated in the display 4a 4b such that it matches the wearer's view of the target 20.

The distance 22 between the target 20 and each of the cameras 6a 6b is measured by the cameras 6a 6b.

As this AR headset 2 does not have eye tracking sensors, the distance 26 between each of the wearer's eyes and each of the displays 4a 4b is determined by a calibration procedure. The calibration procedure also involves the determination of the relative position between each of the centre point of the sensors of the cameras 6a and 6b and each of the centre point of the wearer's eyes 30a 30b. The interpupillary distance (IPD) is also determined 24, this may also be through the calibration procedure. Alternatively the IPD may be known and input into the AR system by the wearer.

The relative position between the two displays 4a and 4b and the relative position between the two cameras 6a 6b is known from the geometry of the headset 2. This allows the determination of the distance 40 between the target 20 and the display and the distance 38 between the target and the wearer's eyes 30a 30b.

The determination of each of these distances allows them to be compared to the origin of a coordinate system 36 on the headset 2. This enables the processor 12 to adjust the position of the image on the display such that the position of the image on the display for each of the eyes is matched to the wearer's view of the target.

Throughout the procedure the wearer may move their head relative to the patient 20. By continually measuring the distance 22 throughout the procedure the above calculation can be continually made to adjust the position of the image on the display throughout the procedure such that it matches the wearer's actual real-world view of the target.

In an alternative embodiment of an AR headset having two cameras 6a and 6b and two depth sensors 10a and 10b, the cameras 6a 6b perform the role of capturing the light emitted from the target 20 to form the image in the display 4a 4b. The depth sensors 10a 10b have the role of determining the distance between the patient 20 and the headset 2. The distance between the target 20 and the cameras 6a 6b can be calculated from the distance value determined by the depth sensors and the known spatial relationships.

Figure 3:
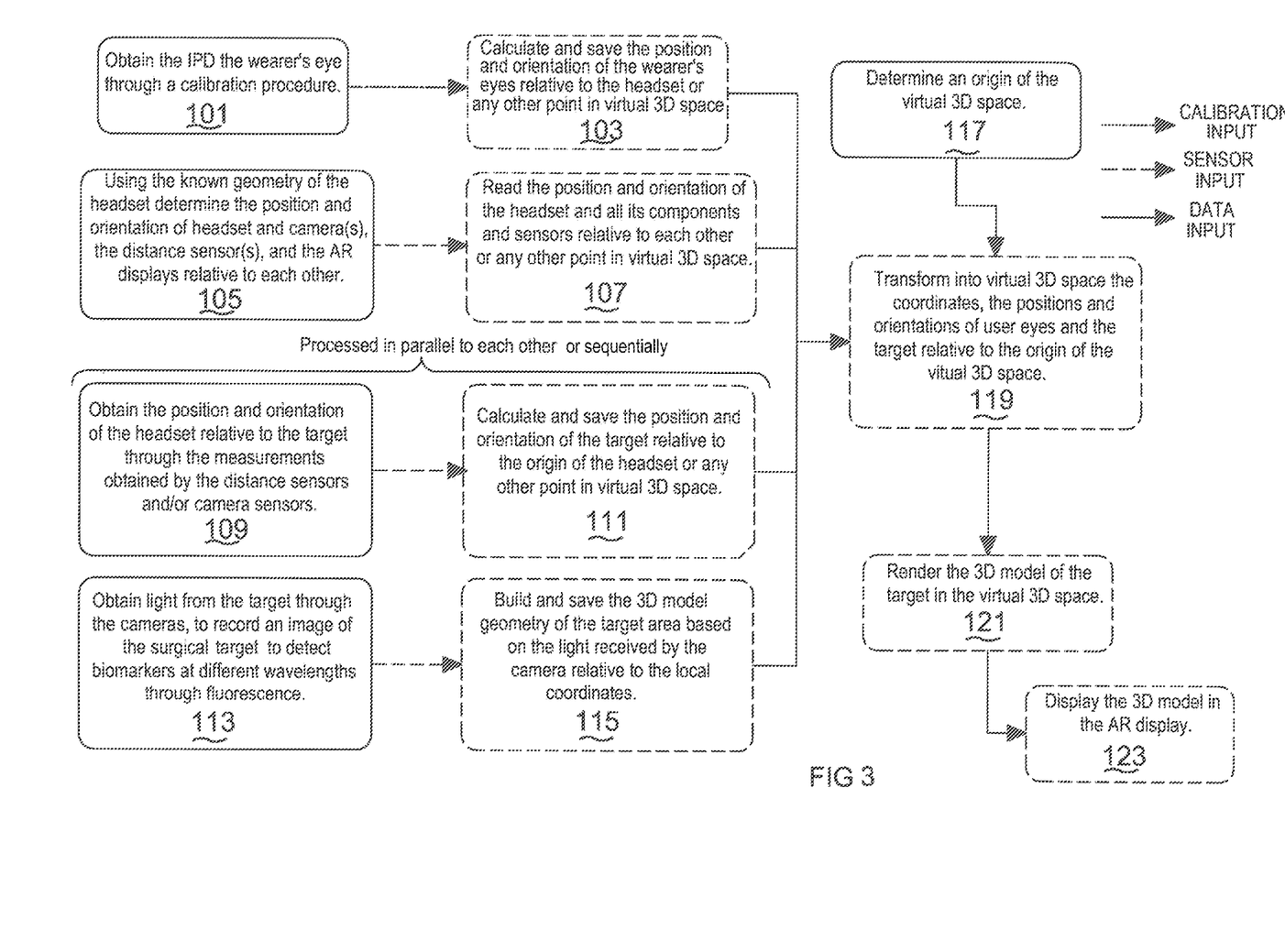
FIG. 3 shows a flow chart of steps performed in displaying a 3D image of a target using an example AR headset as shown in FIG. 2.

The steps performed by either embodiment of the AR system 100 for displaying the image of the target are shown in FIG. 3.

At step 101 the IPD of the wearer's eyes is obtained through a calibration procedure. At step 103 the position and orientation of the wearer's eyes relative to the headset or any other point in virtual 3D space is calculated and saved.

At step 105 using the known geometry of the headset the position and orientation of headset and the camera(s), the depth sensor(s), the eye tracking sensors, and the AR/MR displays relative to each other is determined. This is based on the known geometries as shown in FIGS. 2 and 3. This enables at step 107 for the position and orientation of the headset and all its components and sensors relative to each other or any other point in virtual 3D space to be determined.

Steps 101 to 107 are carried out at the beginning of the medical procedure once the wearer has placed the AR headset on their head. It is taken that these determined values and spatial relationships do not change throughout the medical procedure, such that it is not further necessary to calculate these values throughout the procedure.

Step 109 involves obtaining the position and orientation of the headset relative to the target through the measurements obtained by the camera sensors (as in FIG. 2) and/or by the depth sensors 10a, 10b when present in the headset. The depth sensors may use time of flight, or any known type of measurement used to determine distance. The cameras 6a 6b may use vSLAM, odometry, mapping, localization techniques or any known method for determining distance through image sensors. At step 111 the position and orientation of the target relative to the origin of the headset or any other point in virtual 3D space are calculated and saved.

Step 113 involves obtaining light from the target through the cameras, to record an image of the surgical wound to detect biomarkers at different wavelengths through fluorescence. At step 115 the 3D model geometry of the target area can be built and saved based on the light received by the camera relative to the local coordinates. The local coordinates may be the same point on the headset or point in virtual space that the other positions and orientations are determined from.

At step 117 the origin of the virtual 3D space is determined. As shown in FIG. 2 this is the point 36 on the headset positioned between the two displays 4a and 4b. This virtual 3D space can be the same point by which the position and orientation of the headset, wearer's eyes and the 3D model are determined with respect to in steps 103, 107, 111, 115. This results in step 119 where the position and orientations of the wearer's eyes, and the target are transformed into virtual 3D space relative to the origin of the virtual 3D space.

At step 121 the 3D model of the target in virtual 3D space is then rendered.

At step 123 the rendered 3D model is then displayed in the display 4a 4b of the AR headset 2. This enables the 3D model of the target to be displayed automatically with the perspective view for each eye of the wearer.

Steps 109, 111 are performed throughout the medical procedure. This may be continually or at fixed points in time. This is because the wearer's head, and hence the AR headset 2 may move throughout the procedure. This will lead to the value determined in step 109 changing throughout the procedure, as illustrated and described with reference to FIGS. 8 to 11 herein.

Step 113 and 115 may also be performed throughout the medical procedure. This may be continually or at fixed points in time. This is due to the fact that the light detected by the camera may change throughout the procedure, as the medical procedure progresses. Steps 109, 111, and 113 and 115 may be run in parallel throughout the medical procedure.

As a result of this, steps 119, 121 and 123 may also be carried out throughout the medical procedure to take into account the updated data obtained from steps 109 to 115.

FIG. 4 shows a further embodiment of an AR headset 2, including depth sensors 10a, 10b and two eye tracking sensors 18a and 18b. The spatial relationships are shown in FIG. 4. In this embodiment, the distance 44 between the eye tracking sensors 18a 18b and the wearer's eyes 30a 30b are measured using the eye tracking sensors 18a 18b. This enables an accurate position and orientation of the wearer's eyes to be determined throughout the medical procedure. The distance 46 between the eye tracking sensors and the display is also determined. This may be either determined using the eye tracking sensors 18a 18b or may be a known spatial relationship based on the geometry of the headset.

The determination of the distance 44 and tracking of the wearer's eyes can be performed throughout the medical procedure. This enables the image of the target in the display to be updated to take into account the movement of the wearer's eyes. This can provide a more accurate matching of the wearer's view of the target to the image displayed on the AR display as the position of the wearer's eyes may be known throughout the procedure. The eye tracking sensor may determine the position of the wearer's eyes continually throughout the medical procedure or at fixed intervals in time. The eye tracking sensor may determine the position of the wearer's eyes at the same time as when the distance to the target is measured. Use of the eye tracking sensors can provide a higher level of precision than without eye tracking sensors, this may allow a higher precision to be achieved as it takes into account changes in the wearer's eye movement. This is compared to the headset in FIG. 2 where a reduced precision can be obtained. In addition, if the position of the headset moves on the wearer's head the eye tracking sensors can correct for this movement performing a recalibration. In this way, having eye tracking sensors removes the need for an initial calibration to be performed such as through using a calibration reference at the beginning of the procedure.

The eye tracking sensor may use near-infrared technology along with a camera (or other type of optical sensor) to track direction of the gaze of the wearer's eyes. This may involve using Pupil Center Corneal Reflection (PCCR). Alternatively, the eye tracking sensor may utilize electro-oculography technology. This involves dry electrodes measuring the electrical potential of the skin around the eyes. Miniaturized electronics interpret electrical signals to calculate the eye movements. The sample rate may be around 256 samples per second, although this will depend on the type of camera. Alternatively, any type of eye tracking technology that is known may be used.

Figure 5:
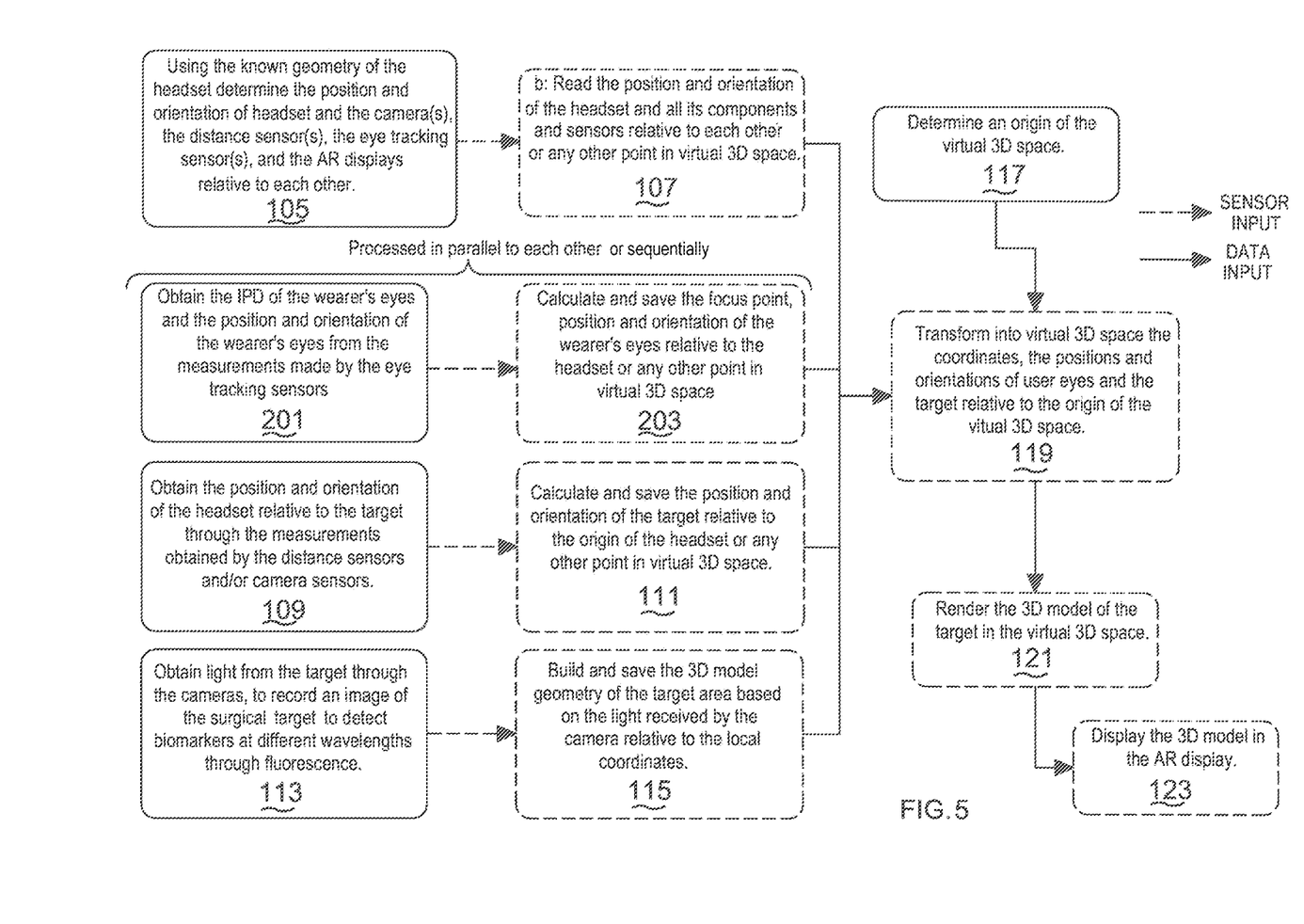
FIG. 5 shows a flow chart of steps performed in displaying a 3D image of a target using an example AR headset as shown in FIG. 4.

The steps performed by the AR system 100 of FIG. 4 in displaying the image of the target are shown in FIG. 5. Each of the steps in FIG. 5 that are identical to the steps in FIG. 3 is denoted by the same reference numeral.

Steps 201 and 203 in FIG. 5 are different to steps 101 and 103 in FIG. 3. Step 201 involves obtaining the IPD of the wearer's eyes, and the position and orientation of the wearer's eyes from the measurements made by the eye tracking sensors. Step 203 then involves calculating and saving the focus point, position and orientation of the wearer's eyes relative to the headset or any other point in virtual 3D space. This is based on the measurements made by the eye tracking sensors 18*a* 18*b*.

Steps 201 and 203 are carried out throughout the medical procedure as outlined above. This is then fed into step 119 to render and display the corrected image in steps 121 and 123.

Figure 6:
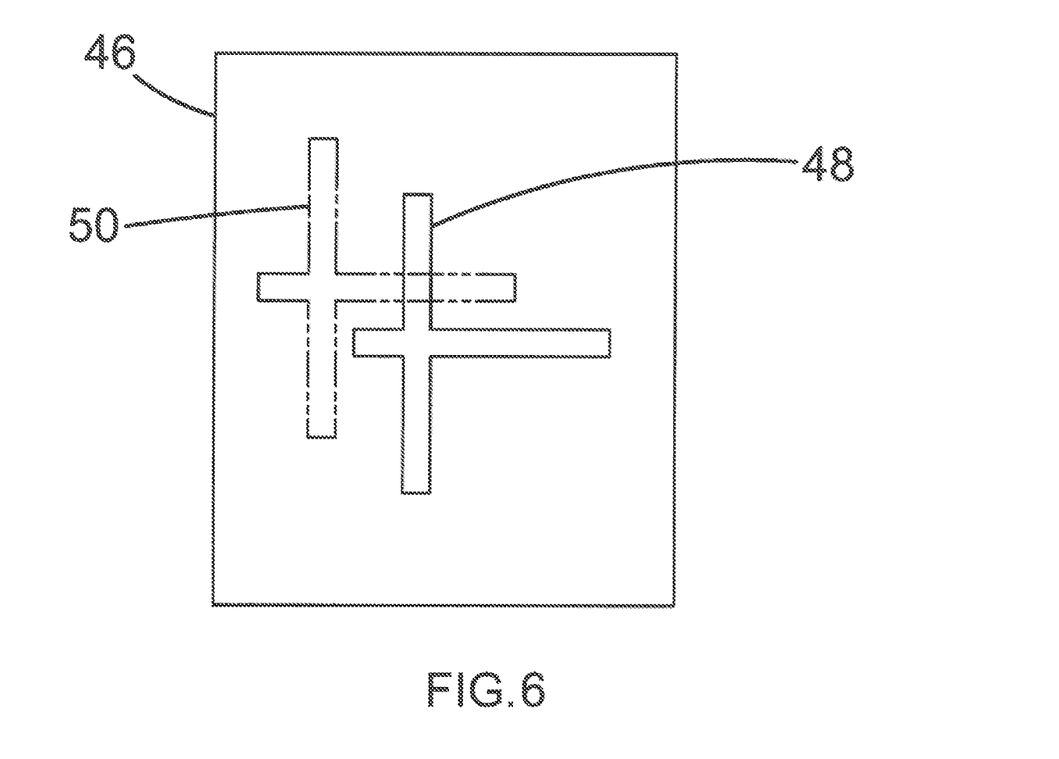
FIG. 6 shows a reference for a calibration procedure for use in displaying a 3D image of a target using an example AR headset.

As described above when the AR headset 2 does not have an eye tracking sensor to determine the position of the wearer's eyes, such as the headset shown in FIG. 2, it is necessary to carry out a calibration procedure. This may involve the wearer viewing an external calibration reference 46 as shown in FIG. 6. The calibration reference in FIG. 6 is a reference pattern 48. The actual position of the reference pattern 48 is shown in FIG. 6. The uncorrected image of the reference pattern is also shown denoted by 50. Adjustments are then made until the position of the image of the reference pattern 50 is matched to the wearer's view of the reference pattern 48. This may involve the wearer manually adjusting parameters of the image generation such that the image of the reference pattern 50 is moved to overlay their view of the reference pattern 48. This calibration enables the processor to determine the position of the wearer's eyes relative to the origin of a coordinate system, such as a point on the headset.

Further details on how the alignment of the image on the display is corrected will now be described. This is one such example of how this may be achieved and alternative algorithms and methods may instead be applied.

To correct the image on the display based on the wearer's perspective view the camera's parameters including position and orientation and its optical properties are determined. The 3D information of the target, and the mismatch between the images displayed for each eye are also determined to correct the image, in order to have a depth perception of the virtual object. The camera's position and orientation is determined based on steps 109 and 111. The 3D information of the target is determined based on steps 113 and 115. The mismatch between the images displayed for each eye is detailed based on steps 101, 103, 201, 203, 105, 107, 109 and 111.

The camera's parameters are determined based on intrinsic parameters representing the optical properties of the camera, and extrinsic parameters representing the position and orientation of the camera.

The intrinsic parameters represent the optical properties and can be estimated using the pinhole camera model. These include, the focal length of the camera, the aspect ratio of the plane where the camera's view is projected (i.e. the display), and the location of the image center (its principal point) where the optical axis intercepts the image plane.

The position and orientation of the camera is determined by calculating its pose. This may be calculated using the sensors on the camera, for instance the depth sensor.

Based on the calibration parameters, 3D points are calculated, which can be projected on 2D image coordinates.

The initial intrinsic and extrinsic matrix should be estimated for a specific headset and user configuration at run time in the calibration. There are different calibration procedures that use manual interactions to collect 3D and 2D correspondences by manually aligning a world reference point to 2D points displayed on the screen. For exemple, Tuceryan and Navad[a] introduced SPAAM (Single Point Active Alignment Method). They propose collecting individual 2D-3D point correspondences one at the time and then solving for all projection parameters at the same time. To do so, the user must align a 2D symbol (circle or cross) with a 3D object. The headset and 3D object are spatially tracked. Once we have at least 6 correspondences, they are used to create and solve a system of linear equation as an initial estimate of the parameters. Tracking the eyes position, these values can instead be computed automatically in runtime.

[a] Tuceryan, Mihran & Navab, Nassir. (2000). Single point active alignment method (SPAAM) for optical see-through HMD calibration for AR. 149-158. 10.1109/ISAR.2000.880938.

We will now describe how the disparity of each camera may be calculated. This is then used to create a depth map using the stereo camera system. The calculation of the disparity is defined with the following terms and formula:

$O_l$=position of left eye
$O_r$=position of right eye
P=position of target
f=focal length
B=base length
$x_l$ and $x_r$=point in the left or right image respectively
Z=distance to target In a stereo system, the disparity is defined by $d=x_l-x_r$ and therefore:

$$d = f\frac{B}{Z}$$

Thus, the disparity is inversely proportional to the distance to the target. By knowing the distance to the target throughout the medical procedure and the position of the wearer's eyes it is possible to update the alignment of generated 3D model of the target (the image) such that it is at the correct alignment for both of the wearer's eyes. This is further based on the estimated camera parameters as described above.

Figure 7:
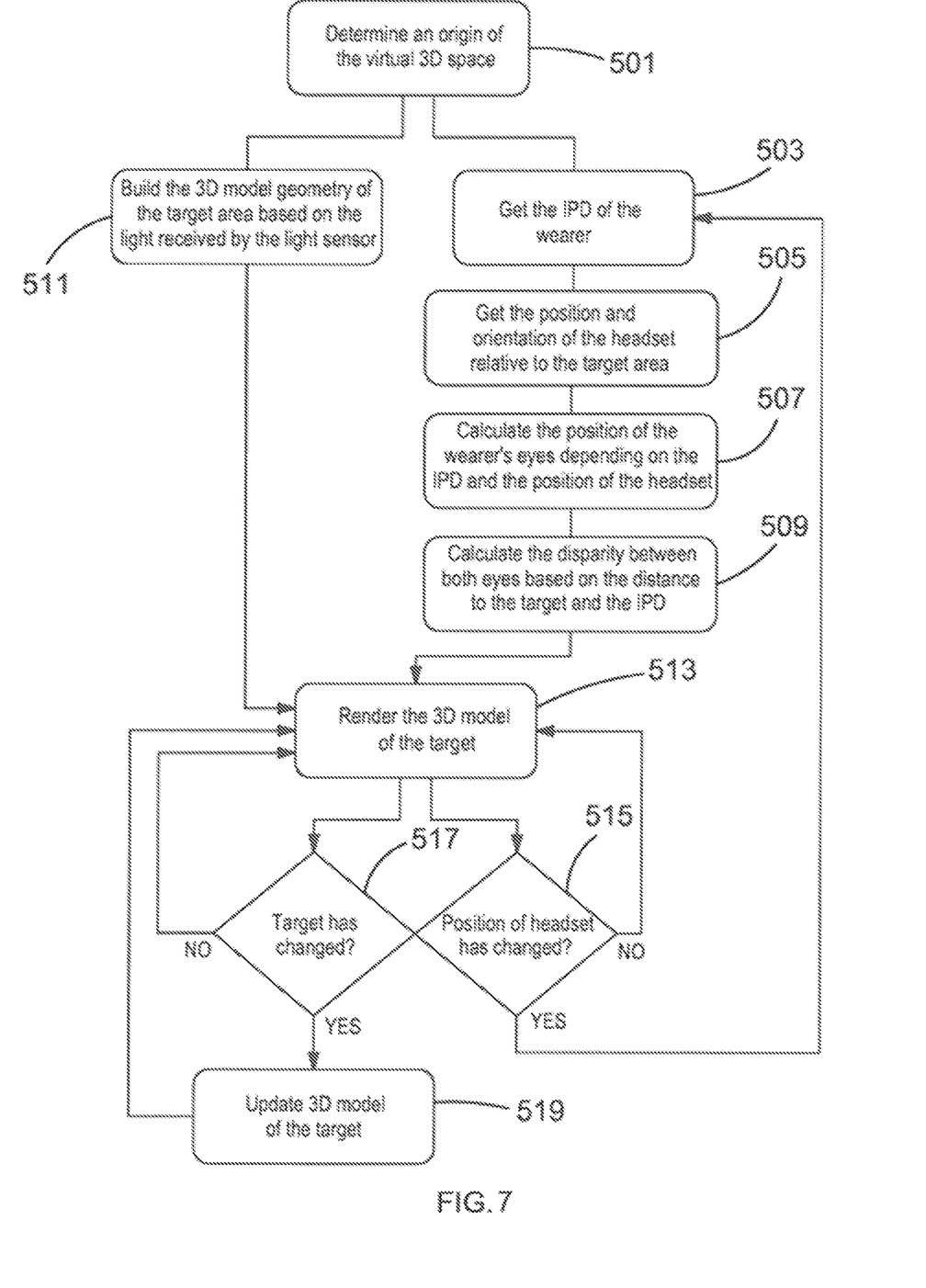
FIG. 7 shows a further flow chart of steps performed in displaying a 3D image of a target using an example AR headset as shown in FIG. 2 or 4

FIG. 7 shows a further flow chart of the method of adjusting the position of the image in the display for the headset of FIG. 2 or 4.

At step 501 the origin in the 3D virtual space is determined. This is set to be a position from which the spatial relationships are determined.

At step 503 the IPD of the wearer is determined. This might be manually inputted, such as being entered by the wearer. Alternatively, where the headset has eye tracking sensors this may be determined through the eye tracking sensors.

At step 505 the position and orientation of the headset relative to the target is determined. This can be through receiving light from the target through the camera and analysing this light as explained above.

At step 507 the position of the wearer's eyes is determined based on the IPD and the position of the headset. This might be determined using a calibration procedure before the medical procedure. Alternatively, it might be through using the eye tracking sensors to determine the distance between the wearer's eyes and the headset.

At step 509 the mismatch required for the wearer to perceive the images from the stereo system as a 3D object between both eyes is determined based on the distance to the target and the IPD. The distance to the target is determined through the depth sensor and/or camera.

At step 511 a 3D model geometry of the target is built based on the light received at the camera. Step 511 can be carried out in parallel whilst steps 503 to 509 are being performed.

Step 513 involves rendering the 3D model of the target. This is based on the 3D model built in step 511 and it is rendered based on the calculated mismatch in step 509, and the position the headset relative to the target area as in step 505.

At step 515 a determination is made whether the position of the headset has changed. If it has steps 503 to 513 are then repeated. If it has not the same 3D model is rendered based on the previous calculated values.

At step 517 it is determined if the target has changed. If it has step 519 is performed to update the 3D model of the target with the updated 3D model rendered in step 513.

Figure 8:
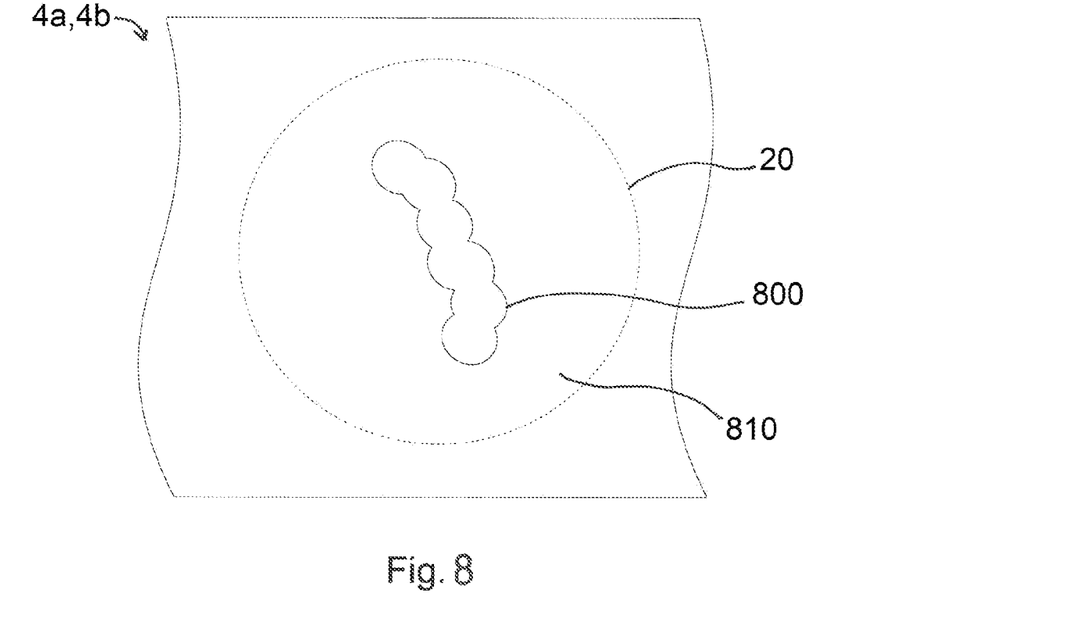
FIG. 8 illustrates a top view of a target composited with a 3D image by an AR headset according to the prior art.
Figure 9:
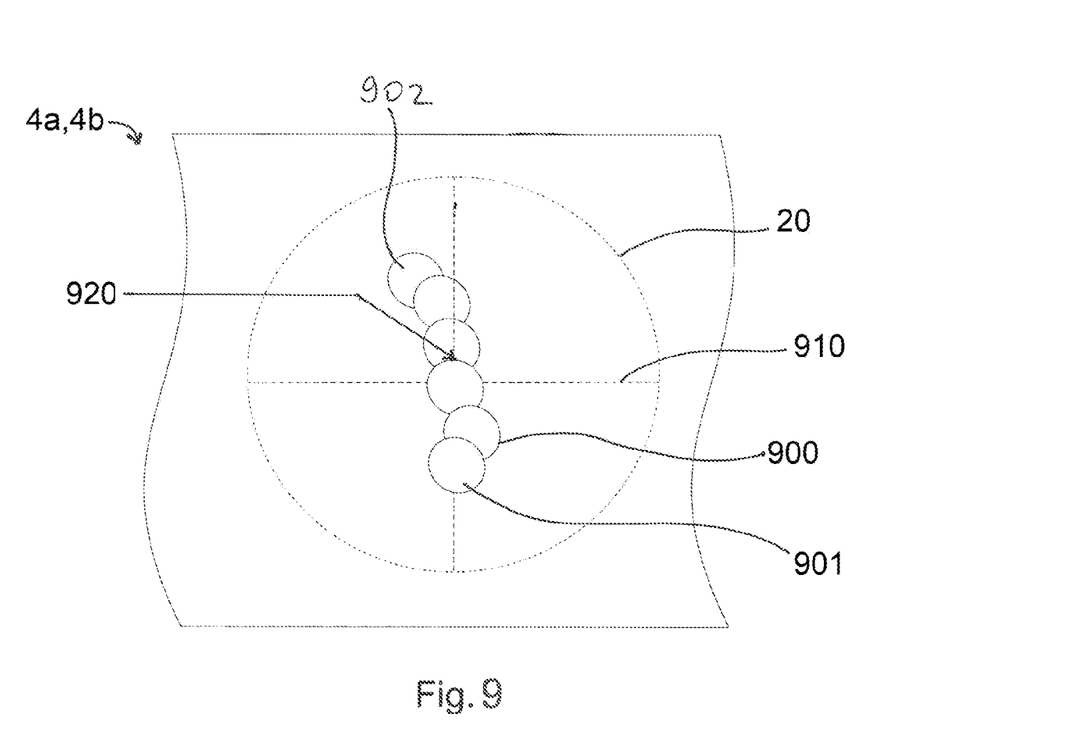
FIG. 9 illustrates a top view of a target composited with a 3D image by an AR headset according to the steps of FIG. 7.
Figure 10:
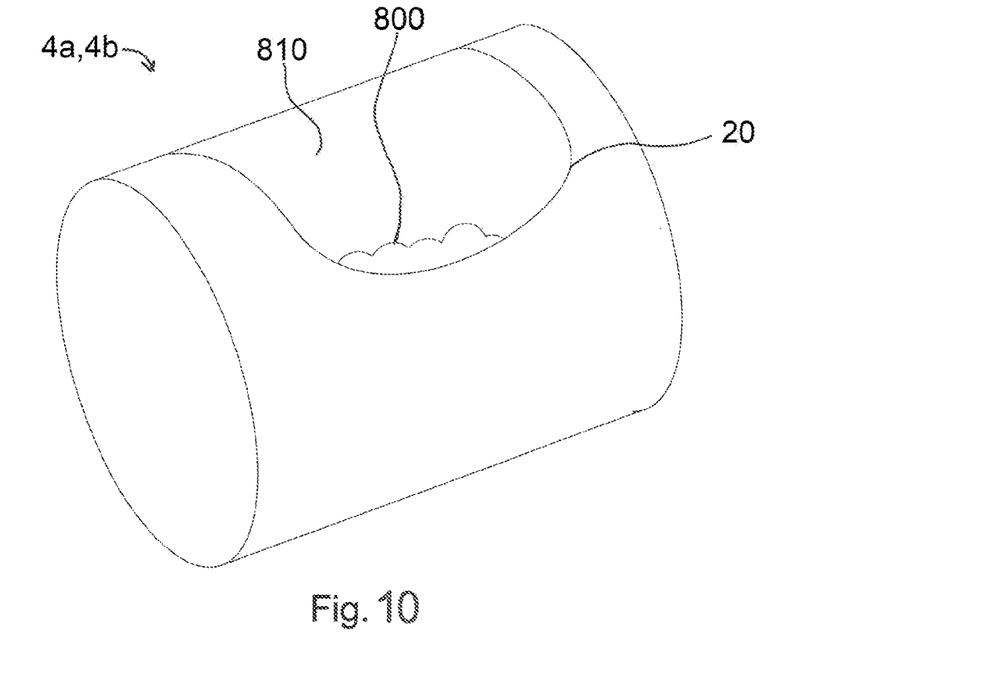
FIG. 10 illustrates a perspective view of the target of FIG. 8 according to the prior art after a viewpoint rotation.
Figure 11:
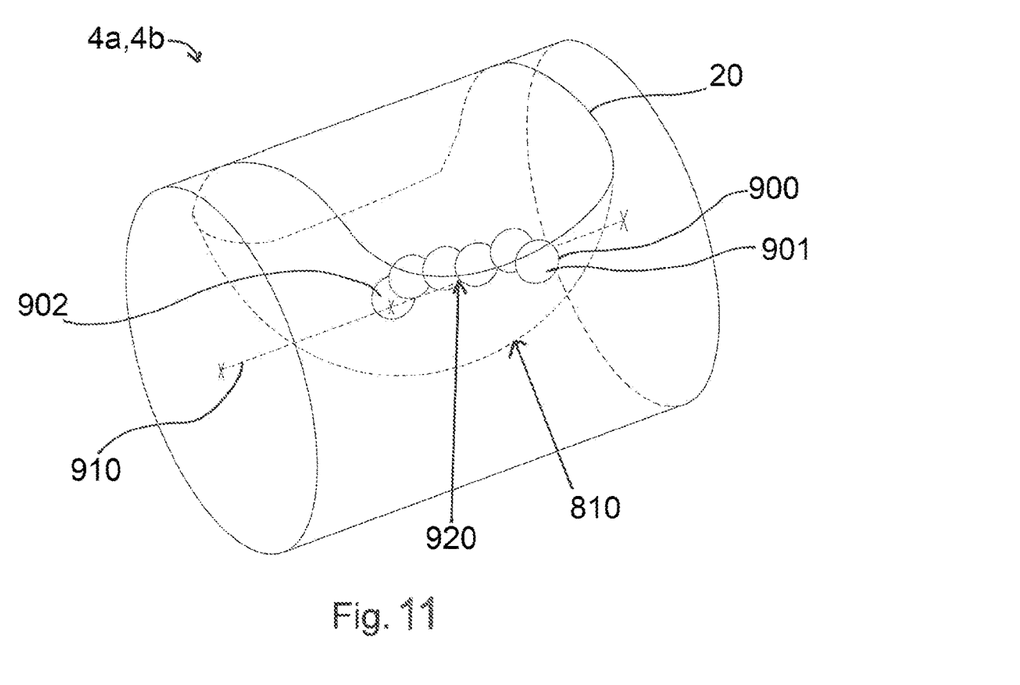
FIG. 11 illustrates a perspective view of the target of FIG. 9 according to the steps of FIG. 7.

With reference to FIGS. 8 to 11 now, wherein like reference numerals designate like features, the method of adjusting the position of an image in the AR system 100 described herein is illustrated in two sets of views of the target 20, respectively based on a distance determination relative to the target in FIGS. 8 and 10 and, by contrast, based on a depth determination relative to the agent in FIGS. 9 and 11.

In these examples, the target 20 is a portion of a patient limb containing an optical contrast agent, such as ICG, observable through the transparent displays 4a, 4b of the headset 2. The limb contains a plurality of cancer nodules biomarked by the contrast agent.

FIGS. 8 and 10 show a representation of a 3D model 800 of the nodules in the target 20 rendered and overlaid in the transparent displays 4a, 4b according to the principles described herein, based solely on a determination of the distance between the headset 2 and the target 20, wherein the depth of the agent relative to the target surface is not determined.

The 3D model 800 is rendered without any volume information and therefore appears flat wherein, upon changing the orientation of the viewer's field of view from the top down aspect shown in FIG. 8 to the perspective aspect shown in FIG. 10 during the medical procedure, the 3D model 800 remains overlaid on the target 20 but its volume and scale cannot be observed on the displays 4a, 4b relative to the adjacent limb volume 810.

FIGS. 9 and 11 show a representation of a 3D model 900 of the same nodules in the target 20 rendered and overlaid in the transparent displays 4a, 4b according to the principles described herein, now based on a determination of the distance between the headset 2 and the agent within the target 20, wherein the depth of the agent relative to the target surface is either determined from a secondary determination of the distance between the headset 2 and the target 20 and a corresponding computation between both distances, or input to the computer 12 if it has been determined by other means previously, e.g. an MRI scan.

The 3D model 900 is rendered with volume information and appears as a plurality of distinct nodules between end nodules 901, 902, moreover each with a respective depth of location relative to the target surface, represented in FIGS. 9 and 11 by a three-dimensional coordinate system centred about the limb main axis 910. The adjacent limb volume 810 is conferred an observable depth relative to the example of FIGS. 8 and 10, of typically of up to 2 centimetres depending upon the combination of fluorophore and light source used by the system 100

Upon changing the orientation of the viewer's field of view from the top down aspect shown in FIG. 9 to the perspective aspect shown in FIG. 11 during the medical procedure, the 3D model 900 remains overlaid on the target 20 and its volume and scale can be observed on the displays 4a, 4b relative to the adjacent limb volume 810, best illustrated in FIGS. 9 and 11 by the intersection 920 of the 3D model with the limb main axis 910.

Another example could be a local metastasis or spreading of abdominal cancer. Various cancer nodules are spread under the skin surface of a belly. Invisible at normal sight, our AR headset would enable a surgeon to see the location and a much better part of the size and form of the cancer nodule under the skin. This without external cameras where he/she has to draw on the patient—just simply by looking at the abdomen area.

Accordingly, by using cameras arranged in a stereoscopic setup with a subcutaneous optical marker, a more realistic perception of depth and volume is obtained in the system of the invention, in real time in direct sight of the wearer: the size, exact location and, potentially, still more information such as subject type, can be defined and rendered in realtime. These advantages are not considered possible with other approaches, as single camera-based systems and non-NIR-based systems perceive only target surfaces and make determinations and render 3D model based upon same, rather than the subcutaneous subject, like the cancer nodules of the example, that are the subject of real surgical interest.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

Although FIGS. 2 and 4 show the spatial relationships that are determined, calculated or known, any other type of spatial relationships may be determined according to the present invention. All that is required is that the relationships between the headset, wearer and target can be determined such that the position on the image in the display can be corrected based on the view of each of the wearer's eyes.

Triangulation methods may be used to create the 3D model from the images obtained from the imaging means. This may include laser triangulation. This involves the projection of a laser beam onto the surface of the target. The measure of the deformation of the laser ray provides details of the geometry of the target. Alternatively, it may involve using the time of flight of a laser beam. The laser beam is projected onto the surface of the target and then collected by a sensor. The time of travel of the laser between its emission and reception gives the surface's geometrical information. These methods may involve the headset having one or more laser sources that can be used to perform these techniques. Any of the AR headsets shown in the figures may have such a laser source.

Although, it is shown that the eye tracking sensors are used in combination with depth sensor and cameras, the eye tracking sensors could be applied to any of the AR headsets described. Alternatively, the eye tracking sensors may be applied to a AR headset having a plurality of cameras and no depth sensor.

The detection of the image and associated actions are described as being performed by a camera. However, any type of image sensor/image sensing device may be used. The camera may be configured to detected still images or videos.

The AR headset is shown in the Figures as having two displays attached to a housing with two arms (temples). However, it will be understood that the AR headset of the present invention is not limited to such an arrangement, and any convention means of attaching a head mounted display (HMD) to a wearer could be envisaged. This may include using straps that pass around and/or over the head to hold the headset in place. Alternatively, an attachment means that attaches the device over the whole of the top of the head, such as a hat may be used.

The device is discussed in relation to being used during a florescence based guidance medical procedure. However, it may be used in any type of medical procedure where it the aim is to detect radiation from the body or tissue of a patient to generate an image. It may also be used outside of medical procedures. For instance, it might find use in other industries where it is necessary to correct the position of an image on a display such that it matches the wearer's view. Such an industry may be architecture or construction.

The processor may be a processor for executing instructions in a data processing device. Instructions may be stored in a memory, for example. Processor may include one or more processing units (e.g., in a multi-core configuration) for executing instructions. The instructions may be executed within a variety of different operating systems on the data processing device, such as UNIX, LINUX, embedded Linux, Microsoft Windows®, etc. More specifically, the instructions may cause various data manipulations on data stored in memory (e.g., create, read, update, and delete procedures). It should also be appreciated that upon initiation of a computer-implemented method, various instructions may be executed during initialization. Some operations may be required in order to perform one or more methods described herein, while other operations may be more general and/or specific to a particular programming language (e.g., C, C#, C++, Java, Python, R, Matlab or other suitable programming languages, etc.).

The invention claimed is:

1. An augmented reality, AR, system for monitoring a target in a medical procedure, comprising:
   an optical contrast agent within the target;
   at least one light source for illuminating the target, the at least one light source having a wavelength adapted to excite the optical contrast agent;
   an AR headset comprising:
   imaging means configured to detect light from at least the optical contrast agent within the target;
   a near-eye display positioned between a wearer's eyes and the target, the display configured to display an image of the at least optical contrast agent based on the light detected by the imaging means, wherein the image overlays a wearer's view of the target through the near-eye display;
   a depth sensor, configured to determine a distance between the headset and the target throughout the medical procedure; and
   a processor, configured to:
      determine a mismatch between the image of the target obtained from the imaging means and the wearer's view of the target based on the value of the distance measured by the depth sensor, a distance between a surface of the target and the optical contrast agent, and a position of the wearer's eyes;
      determine the mismatch required for the wearer to perceive the images from the imaging means as a 3D object/volume/shape from the determined distance and the position of the wearer's eyes;
      adjust the position of the image on the display such that it is corrected based on the determined mismatch such that the image matches the wearer's view of the target; and
      repeat the determination of the mismatch and the adjustment of the position of the image throughout the medical procedure to take into account changes in the distance measured by the depth sensor throughout the medical procedure.

2. The AR system according to claim 1, wherein the processor is further configured to determine the mismatch between the image of the target obtained from the imaging means and the wearer's view of the target by being configured to:
   assign a position in space to act as an origin of a coordinate system;
   generate a 3D model of the optical contrast agent within the target based on the light detected by the imaging means;
   determine the position and orientation of the target relative to the coordinate system origin based on the distance measured by the depth sensor;
   determine the position of the wearer's eyes relative to the coordinate system origin; and
   determine the position and orientation of the headset relative to the coordinate system origin.

3. The AR system according to claim 2, wherein the position and orientation of the headset relative to the coordinate system origin is the position and orientation of at least one of the near-eye display, the depth sensor and the imaging means.

4. The AR system according to claim 2, wherein the processor is further configured to adjust the position of the image on the display such that it is corrected based on the determined mismatch by being configured to:
  set the position of the 3D model of the target relative to the coordinate system origin;
  render the 3D model of the target to form the adjusted image based on the determined positions and orientations of the target, and headset and the position of the wearer's eyes; and
  display the adjusted image on the display.

5. The AR system according to claim 1, wherein the imaging means comprises a plurality of cameras arranged into a stereoscopic imaging means.

6. The AR system of claim 5, wherein the processor is further configured to determine the mismatch between the image of the target obtained from the camera and the wearer's view of the target by being configured to:
  determine the mismatch required for the wearer to perceive images from the stereoscopic imaging means as a 3D object from the determined distance and the position of the wearer's eyes.

7. The AR system according to any claim 1, wherein the depth sensor is a time of flight depth sensor, a stereo sensor setup, a LIDAR sensor, a RADAR sensor or a multi-view geometry setup, or a multi-sensor setup.

8. The AR system according to claim 1, wherein the imaging means comprises the depth sensor.

9. The AR system according to claim 1, wherein the optical contrast agent is excitable by, and the light source has, a wavelength in the range 750 nm to 2500 nm.

10. The AR system according to claim 1, wherein the optical contrast agent is selected from the group comprising a natural metalloprotein, an engineered metalloprotein and a fluorophore.

11. The AR system according to claim 10, wherein the fluorophore is selected from the group comprising single-walled carbon nanotubes (SWNTs), high-pressure carbon monoxide conversion SWNTs (HiPCO-SWNTs), cyanine dyes, fluorophores with donor-acceptor-donor (D-A-D) scaffolds, aggregation-induced emission (AIE) particles, conjugated polymers, quantum dots and rare earth nanomaterials (RENPs).

12. A method of adjusting the position of an image in an augmented reality (AR) system for use in a medical procedure, the AR system comprising an optical contrast agent, at least one light source, an AR headset with stereoscopic imaging means, depth sensor and a processor, the method comprising:
  illuminating a target containing the optical contrast agent with the at least one light source, the at least one light source having a wavelength suitable for exciting the optical contrast agent;
  detecting light from the excited optical contrast agent in the target with the stereoscopic imaging means;
  determining a distance between the headset and the target with depth sensor throughout a medical procedure;
  displaying on a near-eye display of the AR headset positioned between a wearer's eyes and the target, an image of the target based on the detected light, wherein the image overlays a wearer's view of the target through the near-eye display, through the steps of:
  determining a mismatch between the image of the target obtained from the imaging means and the wearer's view of the target based on the determined distance, a distance between a surface of the target and the optical contrast agent and a position of the wearer's eyes;
  determine the mismatch required for the wearer to perceive the images from the imaging means as a 3D object/volume/shape from the determined distance and the position of the wearer's eyes; and
  adjusting the position of the image on the display such that it is corrected based on the determined mismatch.

13. The method according to claim 12, wherein the step of determining the mismatch comprises the further steps of:
  assigning a position in space to act as an origin of a coordinate system;
  generating a 3D model of the optical contrast agent within the target based on the light detected by the imaging means;
  determining the position and orientation of the target relative to the coordinate system origin based on the distance measured by the depth sensor;
  determining the position of the wearer's eyes relative to the coordinate system origin; and
  determining the position and orientation of the headset relative to the coordinate system origin.

14. The method according to claim 12, wherein the imaging means comprises a plurality of cameras arranged into a stereoscopic imaging means, and wherein the step of determining the mismatch comprises the further step of:
  determining the mismatch required for the wearer to perceive images from the stereoscopic imaging means as a 3D object from the determined distance and the position of the wearer's eyes.

15. A non-transitory computer readable medium, that when executed on a processor is configured to perform the steps of claim 12.

* * * * *